United States Patent [19]

Gaffar et al.

[11] Patent Number: 5,575,652
[45] Date of Patent: Nov. 19, 1996

[54] PROCESS FOR APPLYING ANTIBACTERIAL ORAL COMPOSITION TO DENTAL IMPLANT AREAS

[75] Inventors: Abdul Gaffar, Princeton; Ralph P. Santarpia, III, Somerset, both of N.J.

[73] Assignee: Colgate Palmolive Company, New York, N.Y.

[21] Appl. No.: 444,071

[22] Filed: May 18, 1995

Related U.S. Application Data

[60] Continuation-in-part of Ser. No. 161,013, Dec. 3, 1993, Pat. No. 5,466,437, which is a division of Ser. No. 961,976, Oct. 16, 1992, Pat. No. 5,294,431, which is a division of Ser. No. 398,592, Aug. 28, 1989, Pat. No. 5,188,821, which is a continuation-in-part of Ser. No. 291,712, Dec. 29, 1988, Pat. No. 4,894,220, and Ser. No. 346,258, May 1, 1989, Pat. No. 5,043,154, which is a continuation of Ser. No. 8,901, Jan. 30, 1987, abandoned, said Ser. No. 291,712, is a continuation-in-part of Ser. No. 8,901.

[51] Int. Cl.⁶ .................. A61K 5/00; C08L 1/26; C09J 3/04; A61C 5/00
[52] U.S. Cl. .................. 433/173; 106/35; 433/215; 523/120
[58] Field of Search .................. 106/35; 523/120; 433/173, 215; 424/49–58

[56] References Cited

U.S. PATENT DOCUMENTS

| | | | |
|---|---|---|---|
| 683,075 | 9/1901 | Schneider . | |
| 2,505,028 | 4/1950 | Boeger | 128/215 |
| 4,252,525 | 2/1981 | Child | 433/173 |
| 4,373,036 | 2/1983 | Chang et al. | 523/120 |
| 4,485,090 | 11/1984 | Chang | 424/52 |
| 4,521,551 | 6/1985 | Chang et al. | 523/120 |
| 4,551,135 | 11/1985 | Gorman et al. | 433/90 |
| 4,725,234 | 2/1988 | Ethridge | 433/215 |
| 4,801,263 | 1/1989 | Clark | 433/90 |
| 4,941,227 | 7/1996 | Sussman | 15/167.1 |
| 5,242,301 | 9/1993 | Hickey et al. | 433/141 |
| 5,372,503 | 12/1994 | Elia | 433/215 |
| 5,397,235 | 3/1995 | Elia | 433/173 |

*Primary Examiner*—Shep K. Rose
*Attorney, Agent, or Firm*—Robert L. Stone; Paul Shapiro

[57] ABSTRACT

An oral gel composition suitable for application to teeth and gums, particularly of people having dental implants. The gel composition contains an aqueous orally acceptable gel vehicle, a substantially water-insoluble noncationic antibacterial antiplaque agent, such as 2,4,4'-trichloro-2'-hydroxyldiphenyl ether (triclosan) and an antibacterial-enhancing agent which enhances delivery of said antibacterial agent to, and retention thereof on, oral surfaces. The gel composition is extruded from a syringe into contact with a dental implant area thereby causing the composition to be delivered to and retained on the dental implant area.

17 Claims, No Drawings

PROCESS FOR APPLYING ANTIBACTERIAL ORAL COMPOSITION TO DENTAL IMPLANT AREAS

This application is a continuation-in-part of application Ser. No. 08/161,013, filed Dec. 3, 1993, now U.S. Pat. No. 5,466,437, granted Nov. 14, 1995 which is a Division of application Ser. No. 07/961,976, filed Oct. 16, 1992, now U.S. Pat. No. 5,294,431, granted Mar. 15, 1994, which is a Division of application Ser. No. 07/398,592, filed Aug. 28, 1989, now U.S. Pat. No. 5,188,821, granted Feb. 23, 1993 which is a continuation-in-part of application Ser. No. 07/291,712, filed Dec. 29, 1988, now U.S. Pat. No. 4,894,220, granted Jan. 16, 1990, and of application Ser. No. 07/346,258 filed May 1, 1989 and now U.S. Pat. No. 5,043,154, granted Aug. 27, 1991, which are respectively a continuation-in-part and a continuation of application Ser. No. 07/008,901, filed Jan. 30, 1987 now abandoned.

This invention relates to a method using an antibacterial antiplaque oral gel composition. As such it uses a gel composition more viscous than a typical or preferred liquid dentifrice of ancestor application Ser. Nos. 08/161,013; 07/961,976 (now U.S. Pat. No. 5,294,431); and, 07/398,592 (now U.S. Pat. No. 5,188,821). In particular, it relates to applying an oral gel composition containing a substantially water-insoluble noncationic antibacterial agent effective to inhibit oral plaque from a syringe to a dental implant to contact the oral composition with the dental implant and the area of the gums carrying the implant.

Dental plaque is a soft deposit which forms on teeth as opposed to calculus which is a hard calcified deposit on teeth. Unlike calculus, plaque may form on any part of the tooth surface, particularly including at the gingival margin. Hence, besides being unsightly, it is implicated in the occurrence of gingivitis. When dental implants are placed into the gums, there is a tendency for plaque-forming material to be trapped and for plaque to form in increased amount over other tooth-gum interfacial areas.

Accordingly, it is highly desirable to include antimicrobial agents which have been known to reduce plaque in oral compositions. Frequently, cationic antibacterial agents have been suggested. Moreover, in U.S. Pat. No. 4,022,880 to Vinson et al, a compound providing zinc ions as an anticalculus agent is admixed with an antibacterial agent effective to retard the growth of plaque bacteria. A wide variety of antibacterial agents are described with the zinc compounds including cationic materials such as guanides and quaternary ammonium compounds as well as non-cationic compounds such as halogenated salicylanilides and halogenated hydroxydiphenyl ethers. The noncationic antibacterial antiplaque halogenated hydroxydiphenyl ethers, triclosan, has also been described in combination with zinc citrate trihydrate in European Patent Publication 0161,899 to Saxton et al. Also, in European Patent Publication 0271,332 to Davis, mouthwash containing triclosan and in a carrier system containing a solubilizing agent such as propylene glycol is disclosed.

The cationic antibacterial materials such as chlorhexidine, benzethonium chloride and cetyl pyridinium chloride have been the subject of greatest investigation as antibacterial antiplaque agents. However, they are generally not effective when used with anionic materials. Noncationic antibacterial materials, on the other hand, can be compatible with anionic components in an oral composition.

However, oral compositions typically are mixtures of numerous components and even such typically neutral materials as humectants can affect performance of such compositions. Moreover, when oral compositions are applied to the teeth and gums of individuals having areas of high plaque formation at dental implant sites, it is important that they be effective compositions, applied in an effective manner for the desired purpose and substantially free of undesirable side effects.

Moreover, even noncationic antibacterial antiplaque agents may have limited antiplaque effectiveness with commonly employed materials such as polyphosphate anticalculus agents which are disclosed together in British Patent Publication 22 00551 of Gaffar et al and in EP 0251591 of Jackson et al. In commonly assigned Ser. No. 398,605 filed on Aug. 25, 1989, titled "Antibacterial, Antiplaque Anticalculus Oral Composition", it is shown that the antiplaque effectiveness is greatly enhanced by including an antibacterial-enhancing agent (AEA) which enhances the delivery of said antibacterial agent to, and retention thereof on, oral surfaces and providing optimized amounts and ratios of polyphosphate and AEA.

Further, even when polyphosphate anticalculus agent is not present as shown in patent applications commonly assigned, 398, 606; 398,566; and 399,669 each filed on Aug. 25, 1989, antiplaque effectiveness on soft oral tissue is optimized in dentifrices containing the noncationic antibacterial agent and said AEA.

Additionally, although prior oral compositions of the type described are generally suitable for application to teeth and gums by brushing, or rinsing such delivery means they can be insufficient for individuals subject to high plaque formation at dental implant sites.

Dental implants have a different surface than natural teeth for accumulation of plaque. They are typically composed of three portions. First, there is titanium alloy fixture which is affixed to alevolar bone. Second, there is titanium alloy collar transmucsal abutment at the gingiva mucosa surface where plaque formation tends to be greatest. Third, there is a porcelain prosthesis which is attached to the collar.

It is an advantage of this invention that an oral gel composition is employed in which substantially water-insoluble noncationic antibacterial agent is solubilized to provide substantial antiplaque effectiveness in the presence of said AEA upon direct application to dental implant sites including areas of the gums carrying the implants, in the oral cavity.

It is an advantage of this invention that the said AEA enhances the delivery and retention of a small but effective antiplaque amount of the antibacterial agent on teeth and on soft oral tissues.

It is a further advantage of this invention that an antiplaque oral composition which is effective to reduce the occurrence of gingivitis at the implant sites, is applied by syringe.

Additional advantages of this invention will be apparent from consideration of the following specification.

In accordance with certain of its aspects, this invention relates to a process for attaching, adhering or bonding a plaque-inhibiting antibacterial agent to a dental implant area in the oral cavity which comprises placing an oral gel composition in a dental syringe, which oral gel composition has a viscosity of about $150 \times 10^3$ to about $360 \times 10^3$ cps and comprises in an orally acceptable gel vehicle, an effective antiplaque amount of a substantially water insoluble noncationic antibacterial agent, at least one of an organic surface active agent and a flavoring oil solubilizing material for said antibacterial agent in amount sufficient to dissolve said antibacterial agent in saliva and about 0.005–6% by weight of an antibacterial-enhancing agent which contains at least one delivery-enhancing functional group and at least one organic retention-enhancing group, wherein said delivery-enhancing group enhances delivery of said antibacterial agent to oral surfaces and said retention-enhancing group enhances attachment, adherence or bonding of said antibacterial agent to oral surfaces, wherein said oral gel composition is free of polyphosphate anticalculus agent in an effective anticalculus amount, applying said syringe to a dental implant and extruding said oral gel composition from said syringe onto the surface of said implant including the interface of said dental implant with gum surfaces.

Typical examples of water insoluble noncationic antibacterial agents which are particularly desirable from considerations of antiplaque effectiveness, safety and formulation are:

Halogenated Diphenyl Ethers

2',4,4'-trichloro-2-hydroxy-diphenyl ether (Triclosan)
2,2'-dihydroxy-5,5'-dibromo-diphenyl ether.

Halogenated Salicylanilides

4',5-dibromosalicylanilide
3,4',5-trichlorosalcylanilide
3,4',5-tribromosalicylanilide
2,3,3',5-tetrachlorosalicylanilide
3,3,3',5-tetrachlorosalicylanilide
3,5-dibromo-3'-trifluoromethyl salicylanilide
5-n-octanoyl-3'-trifluoromethyl salicylanilide
3,5-dibromo-4'-trifluoromethyl salicylanilide
3,5-dibromo-3'-trifluoro methyl salicylanilide (Fluorophene)

Benzoic Esters

Methyl-p-Hydroxybenzoic Ester
Ethyl-p-Hydroxybenzoic Ester
Propyl-p-Hydroxybenzoic Ester
Butyl-p-Hydroxybenzoic Ester

Halogenated Carbanilides 3,4,4'-trichlorocarbanilid e
3-trifluoromethyl-4,4'-dichlorocarbanilide
3,3,4'-trichlorocarbanilide Phenolic Compounds (including phenol and its homologs, mono- and poly-alkyl and aromatic halo (e.g. F, Cl, Br, I)-phenols, resorcinol and catechol and their derivatives and bisphenolic compounds). Such compounds include inter alia:

Phenol and its Homologs

Phenol
2 Methyl-Phenol
3 Methyl-Phenol
4 Methyl-Phenol
4 Ethyl-Phenol
2,4-Dimethyl-Phenol
2,5-Dimethyl-Phenol
3,4-Dimethyl-Phenol
2,6-Dimethyl-Phenol
4-n Propyl-Phenol
4-n-Butyl-Phenol
4-n-Amyl-Phenol
4-tert-Amyl-Phenol
4-n-Hexyl-Phenol
4-n-Heptyl-Phenol
2-Methoxy-4-(2-Propenyl)-Phenol (Eugenol)
2-Isopropyl-5-Methyl-Phenol (Thymol)

Mono- and Poly-Alkyl and Aralkyl Halophenols

Methyl-p-Chlorophenol
Ethyl-p-Chlorphenol
n-Propyl-p-Chlorophenol
n-Butyl-p-Chlorophenol
n-Amyl-p-Chlorophenol
sec-Amyl-p-Chlorophenol
n-Hexyl-p-Chlorophenol
Cyclohexyl-p-Chlorophenol
n-Heptyl-p-Chlorophenol
n-Octyl-p-Chlorophenol
O-Chlorophenol
Methyl-o-Chlorophenol
Ethyl-o-Chlorophenol
n-Propyl-o-Chlorophenol
n-Butyl-o-Chlorophenol
n-Amyl-o-Chlorophenol
tert-Amyl-o-Chlorophenol
n-Hexyl-o-chlorophenol
n-Heptyl-o-Chloropenol
p-Chlorophenol
o-Benzyl-p-Chlorophenol
o-Benzyl-m-methyl-p-Chlorophenol
o-Benzyl-m, m-dimethyl-p-Chlorophenol
o-Phenylethyl-p-Chlorophenol
o-Phenylethyl-m-methyl-p-Chlorophenol
3-Methyl-p-Chlorophenol
3,5-Dimethyl-p-Chlorophenol
6-Ethyl-3-methyl-p-Chlorophenol
6-n-Propyl-3-methyl-p-Chlorophenol
6-iso-propyl-3-methyl-p-Chlorophenol
2-Ethyl-3,5-dimethyl-p-Chlorophenol
6-sec Butyl-3-methyl-p-Chlorophenol
2-iso-Propyl-3,5-dimethyl-p-Chlorophenol
6-Diethylmethyl-3-methyl-p-Chlorophenol
6-iso-Propyl-2-ethyl-3-methyl-p-Chlorophenol
2-sec Amyl-3,5-dimethyl-p-Chlorophenol
2-Diethylmethyl-3,5-dimethyl-p-Chlorophenol
6-sec Octyl-3-methyl-p-Chlorophenol
p-Bromophenol
Methyl-p-Bromophenol
Ethyl-p-Bromophenol
n-Propyl-p-Bromophenol
n-Butyl-p-Bromophenol
n-Amyl-p-Bromophenol
sec-Amyl-p-Bromophenol
n-Hexyl-p-Bromophenol
cyclohexyl-p-Bromophenol
o-Bromophenol
tert-Amyl-o-Bromophenol
n-Hexyl-o-Bromophenol
n-Propyl-m,m-Dimethyl-o-Bromophenol
2-Phenyl Phenol
4-Chloro-2-methyl phenol
4-chloro-3-methyl phenol
4-chloro-3,5-dimethyl phenol
2,4-dichloro-3,5-dimethyl phenol
3,4,5,6-tetrabromo-2-methylphenol
5-methyl-2-pentylphenol
4-isopropyl-3-methylphenol
5-chloro-2-hydroxydiphenyl methane

Resorcinol and Its Derivatives

Resorcinol
Methyl-Resorcinol
Ethyl-Resorcinol n-Propyl-Resorcinol
n-Butyl-Resorcinol
n-Amyl-Resorcinol
n-Hexyl-Resorcinol
n-Heptyl-Resorcinol
n-Octyl-Resorcinol
n-Nonyl-Resorcinol
Phenyl-Resorcinol
Benzyl-Resorcinol
Phenylethyl-Resorcinol
Phenylpropyl-Resorcinol
p-Chlorobenzyl-Resorcinol
5-Chloro-2,4-Dihydroxydiphenyl Methane
4'-Chloro-2,4-Dihydroxydiphenyl Methane
5-Bromo-2,4-Dihydroxydiphenyl Methane
4"-Bromo 2,4-Dihydroxydiphenyl Methane Bisphenolic Compounds Bisphenol A
2,2'-methylene bis(4-chlorophenol)
2,2'-methylene bis(3,4,6-trichlorophenol) (hexachlorophene)
2,2'-methylene bis(4-chloro-6-bromophenol)
bis(2-hydroxy-3,5-dichlorophenyl)sulfide
bis(2-hydroxy-5-chlorobenzyl)sulfide The noncationic antibacterial agent is present in the oral gel composition in an effective antiplaque amount, typically about 0.01–5% by weight, generally about 0.01–0.6%, preferably about 0.03–0.3%. The antibacterial agent is substantially water-insoluble, meaning that its solubility is less than about 1% by weight in water at 25° C. and may be even less than about 0.1%.

The preferred halogenated diphenyl ether is triclosan. The preferred phenolic compounds are phenol noncationic antibacterial agents farnesol, nerolidol, bisabolol, phenol, thymol, eugenol, and 2,2'methylene bis(4-chloro-6-bromophenol). The most preferred antibacterial antiplaque compound is triclosan. Triclosan is disclosed in aforementioned U.S. Pat. No. 4,022,880 as an antibacterial agent in combination with an anticalculus agent which provides zinc ions and in German Patent Disclosure 3532860 in combination with a copper compound. In European Patent Disclosure 0278744 it is disclosed in combination with a tooth desensitizing agent containing a source of potassium ions. It is also disclosed as an antiplaque agent in a dentifrice formulated to contain a lamellar liquid crystal surfactant phase having a lamellar spacing of less than 6.0 mm and which may optionally contain a zinc salt in published European Patent Application 0161898 of Lane et al and in a dentifrice containing zinc citrate trihydrate in published European Patent Application 0161899 to Saxton et al.

The antibacterial-enhancing agent (AEA) which enhances delivery of said antibacterial agent to, and retention thereof on, oral surfaces, is employed in amounts effective to achieve such enhancement within the range in the oral gel composition of about 0.05% to about 6%, preferably about 3% to about 6%, more preferably about 4.5% to about 6% by weight. The AEA can contribute to the viscosity of the oral gel composition, and indeed certain AEA's can also provide gelling or thickening characteristics to the gel vehicle of the oral gel composition to such that a viscosity of about $150 \times 10^3$ cps to about $360 \times 10^3$ cps, preferably about $200 \times 10^3$ cps to about $300 \times 10^3$ cps, of the oral gel composition is attained.

AEA polymeric materials of the present invention include those which can be characterized as having utility as dentifrice adhesives or fixatives or dental cements. For example, U.S. Pat. No. 4,521,551 and 4,373,036, each to Chang et al, describe commercially available copolymer of methylvinyl ether-maleic anhydride (Gantrez) as a denture fixative. However, there had not been recognition in the prior art that adhesives, fixatives or cements when applied in water-soluble or water-swellable form together with substantially water-insoluble non-cationic antibacterial antiplaque agents could enhance the antibacterial activity of such agents. Further, in U.S. Pat. No. 4,485,090 to Chang, Gantrez AN copolymer is mentioned among polymeric anionic membrane-forming materials which attach to a tooth surface to form a hydrophobic barrier which reduces elution of a previously applied therapeutic caries prophylactic fluoride compound. Again, there was no recognition that such polymeric material could enhance the antibacterial activity of substantially water-insoluble non-cationic antibacterial antiplaque agents.

The AEA may be a simple compound, preferably a polymerizable monomer, more preferably a polymer, which latter term is entirely generic, including for example oligomers, homopolymers, copolymers of two or more monomers, and the like. The AEA may be natural or synthetic, and water insoluble or preferably water (saliva) soluble or swellable (hydratable, hydrogel forming). It has an (weight) average molecular weight of about 100 to about 1,000,000, preferably about 1,000 to about 1,000,000, more preferably about 2,000 or 2,500 to about 250,000 or 500,000.

The AEA ordinarily contains at least one delivery-enhancing group, which is preferably acidic such as sulfonic, phosphinic, or more preferably phosphonic or carboxylic, or salt thereof, e.g. alkali metal or ammonium, and at least one organic retention-enhancing group, preferably a plurality of both the delivery-enhancing and retention-enhancing groups, which latter groups preferable have the formula $-(X)_n-R$ wherein X is O, N, S, SO, $SO_2$, P, PO or Si or the like, R is hydrophobic alkyl, alkenyl, acyl, aryl, alkaryl, heterocyclic or their inert-substituted derivatives, and n is zero or 1 or more. The aforesaid "inert-substituted derivatives", are intended to include substituents on R which are generally non-hydrophilic and do not significantly interfere with the desired functions of the AEA as enhancing the delivery of the antibacterial agent to, and retention thereof on, oral surfaces such as halo, e.g. Cl, Br, I, and carbo and the like. Illustrations of such retention-enhancing groups are tabulated below.

| n | X | $-(X)_nR$ |
|---|---|---|
| 0 | — | methyl, ethyl, propyl, butyl, isobutyl, t-butyl cyclohexyl, allyl, benzyl, phenyl, chlorophenyl, xylyl, pryridyl, furanyl, acetyl, benzoyl, butyryl, terephthaloyl, etc. |
| 1 | O | ethoxy, benzyloxy, thioacetoxy, phenoxy, carboethoxy, carbobenzyloxy, etc. |
|   | N | ethylamino, diethylamino, propylamido, benzylamino, benzoylamido, phenylacetamido, etc. |
|   | S | thiobutyl, thioisobutyl, thioallyl, thiobenzyl, thiophenyl, thiopropionyl, phenylthioacetyl, thiobenzoyl, etc. |
|   | SO | butylsulfoxy, allylsulfoxy, benzylsulfoxy, phenylsulfoxy, etc. |
|   | $SO_2$ | butylsulfonyl, allylsulfonyl, benzylsulfonyl, phenylsulfonyl, etc. |
|   | P | diethylphosphinyl, ethylvinylphosphinyl, ethylallylphosphinyl, ethylbenzylphosphinyl, ethylphenylphosphinyl, etc. |
|   | PO | diethylphosphinoxy, ethylvinylphosphinoxy, methylallylphosphinoxy, methylbenzylphosphinoxy, methylphenylphosphinoxy, etc. |
|   | Si | trimethylsilyl, dimethylbutylsilyl, dimethylbenzylsilyl, dimethylvinylsilyl, dimethylallylsilyl, etc. |

As employed herein, the delivery-enhancing group refers to one which attaches or substantively, adhesively, cohesively or otherwise bonds the AEA (carrying the antibacterial agent) to oral (e.g. dental implant and implant/gum interfaces) surfaces, thereby "delivering" the antibacterial agent to such surfaces. The organic retention-enhancing group, generally hydrophobic, attaches or otherwise bonds the antibacterial agent to the AEA, thereby promoting retention of the antibacterial agent to the AEA and indirectly on the oral surfaces. In some instances, attachment of the antibacterial agent occurs through physical entrapment thereof by the AEA, especially when the AEA is a cross-linked polymer, the structure of which inherently provides increased sites for such entrapment. The presence of a higher molecular weight, more hydrophobic cross-linking moiety in the cross-linked polymer still further promotes the physical entrapment of the antibacterial agent to or by the cross-linked AEA polymer.

Preferably, the AEA is a anionic polymer comprising a chain or backbone containing repeating units each preferably containing at least one carbon atom and preferably at least one directly or indirectly pendent, monovalent delivery-enhancing group and at least one directly or indirectly pendent monovalent retention-enhancing group geminally, vicinally or less preferably otherwise bonded to atoms, preferably carbon, in the chain. Less preferably, the polymer may contain delivery-enhancing groups and/or retention-enhancing groups and/or other divalent atoms or groups as links in the polymer chain instead of or in addition to carbon atoms, or as cross-linking moieties.

It will be understood that any examples or illustrations of AEA's disclosed herein which do not contain both delivery-enhancing groups and retention enhancing groups may and preferably should be chemically modified in known manner to obtain the preferred AEA's containing both such groups and preferably a plurality of each such groups. In the case of the preferred polymeric AEA's, it is desirable, for maximizing substantivity and delivery of the antibacterial agent to oral surfaces, that the repeating units in the polymer chain or backbone containing the acidic delivery-enhancing groups constitute at least about 10%, preferably at least about 50%, more preferably at least about 80% up to 95% or 100% by weight of the polymer.

According to an embodiment of this invention, the AEA comprises a polymer containing repeating units in which one or more phosphonic acid delivery-enhancing groups are bonded to one or more carbon atoms in the polymer chain. An example of such an AEA is poly (vinyl phosphonic acid) containing units of Formula I:

$$-[CH_2-CH]- \qquad \qquad (I)$$
$$\phantom{-[CH_2-}\backslash$$
$$\phantom{-[CH_2-}PO_3H_2$$

which however does not contain a retention-enhancing group. A group of the latter type would however be present in poly (1-phosphonopropene) with units of Formula II:

$$-[CH-CH]- \qquad \qquad (II)$$
$$\phantom{-[}\backslash \phantom{-}\backslash$$
$$\phantom{-[}CH_3 \phantom{-}PO_3H_2$$

A preferred phosphonic acid-containing AEA for use herein is poly (beta styrene phosphonic acid) containing units of Formula III:

$$-[CH-CH]- \qquad \qquad (III)$$
$$\phantom{-[}\backslash \phantom{-}\backslash$$
$$\phantom{-[}Ph \phantom{-}PO_3H_2$$

wherein Ph is phenyl, the phosphonic delivery-enhancing group and the phenyl retention-enhancing group being bonded on vicinal carbon atoms in the chain, or a copolymer of beta styrene phosphonic acid with vinyl phosphonyl chloride having the units of Formula III alternating or in random association with units of Formula I above, or poly (alpha styrene phosphonic acid) containing units of Formula W:

$$-[CH_2-C]- \qquad \qquad (IV)$$
$$\phantom{-[CH_2-}/\phantom{-}\backslash$$
$$\phantom{-[CH_2}Ph \phantom{-}PO_3H_2$$

in which the delivery-enhancing and retention-enhancing groups are geminally bonded to the chain.

These styrene phosphonic acid polymers and their copolymers with other inert ethylenically unsaturated monomers generally have molecular weights in the range of about 2,000 to about 30,000, preferably about 2,500 to about 10,000, and are, with their methods of preparation disclosed and claimed in concurrently filed application Ser. No. 398, 606, which disclosure is incorporated here. Such "inert" monomers do not significantly interfere with the intended function of any copolymer employed as an AEA herein.

Other phosphonic-containing polymers include, for example, phosphonated ethylene having units of the formula.

$$-[(CH_2)_{14}CHPO_3H_2]n- \qquad \qquad V$$

where n may, for example, be an integer or have a value giving the polymer a molecular weight of about 3,000; sodium poly (butene-4,4-diphosphonate) having units of the formula:

$$-[CH_2-CH]- \qquad \qquad VI$$
$$\phantom{-[CH_2-}\backslash$$
$$\phantom{-[CH_2-}CH_2-CH<(PO_3Na_2)_2,$$

and poly(allyl bis(phosphonoethyl)amine) having units of the formula:

$$+CH_2-CH+ \qquad \qquad VII$$
$$\phantom{+CH_2-}\backslash$$
$$\phantom{+CH_2-}CH_2-N<(C_2H_4(PO_3H_2)_2$$

Other phosphonated polymers include, for example, poly-(allyl phosphono acetate), phosphonated polymethacrylate, etc. and the germinal diphosphonate polymers disclosed in EP Publication 0321233 may be employed herein as AEA's, provided of course that they contain or are modified to contain the above-defined organic retention-enhancing groups.

Although not used in the present invention to coact with polyphosphate anticalculus agent, synthetic anionic polymeric polycarboxylate having a molecular weight of about 1,000 to about 1,000,000, preferably about 30,000 to about 500,000, has been used as an inhibitor of alkaline phosphatase enzyme in optimizing anticalculus effectiveness of linear molecularly dehydrated polyphosphate salts, as disclosed in U.S. Pat. No. 4,627,977 to Gaffar et al. Indeed, in published British Patent Publication 22 00551, the polymeric polycarboxylate is disclosed as an optional ingredient in oral compositions containing linear molecularly dehydrated polyphosphate salts and substantially water-insoluble noncationic antibacterial agent. It is further observed, in the context of the present invention that such polycarboxylate is markedly effective to enhance delivery and retention of the nonionic antibacterial, antiplaque agent to dental surfaces when another ingredient coacts (that is, molecularly dehydrated polyphosphate) ingredient with which the polymeric polycarboxylate coacts is absent in effective anticalculus amounts; for instance, when the ingredient with which the polymeric polycarboxylate coacts is especially the noncationic antibacterial agent.

Synthetic anionic polymeric polycarboxylates and their complexes with various cationic germicides, zinc and magnesium have been previously disclosed as anticalculus agents per se in, for example U.S. Pat. No. 3,429,963 to Shedlovsky; U.S. Pat. No. 4,152,420 to Gaffar; U.S. Pat. No. 3,956,480 to Dichter et al; U.S. Pat. No. 4,138,477 to Gaffar; and U.S. Pat. No. 4,183,914 to Gaffar et al. It is to be understood that the synthetic anionic polymeric polycarboxylates so disclosed in these several patents are operative in the compositions and methods of this invention and such disclosures are to that extent incorporated herein by reference thereto.

The synthetic anionic polymeric polycarboxylate employed herein are well known, being often employed in the form of their free acids or preferably partially or more preferably fully neutralized water soluble or water swellable (Hydratable, gel forming) alkali metal (e.g. potassium and preferably sodium) or ammonium salts. Preferred are essentially straight chain 1:4 copolymers of maleic anhydride or acid with another polymerizable ethylenically unsaturated monomer, preferably methyl vinyl ether (maleic anhydride) having a molecular weight (M.W.) of about 30,000 to about 1,000,000, most preferably about 30,000 to about 500,000. These copolymers are available for example as Gantrez, e.g. AN 139 (M.W. 500,000), A.N. 119 (M.W. 250,000); and preferably S-97 Pharmaceutical Grade (M.W. 70,000), of GAF Corporation.

Other AEA operative polymeric polycarboxylates when containing or modified to contain the said retention-enhancing groups, include those disclosed in U.S. Pat. No. 3,956,480 referred to above, such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Additional operative polymeric polycarboxylates disclosed in above referred to U.S. Pat. No. 4,138,477 and 4,183,914, when containing or modified to contain retention enhancing groups include copolymers of amleic anhydride with styrene, isobutylene or ethyl vinyl ether, polyacrylic, polyitaconic and polymaleic acids, and sulfoacrylic oligomers of M.W. as low as 1,000, available as Uniroyal ND-2.

Suitable generally are retention-enhancing group-containing polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecular either in the alpha-beta position with respect to a carbosyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers ordinarily contain sufficient carboxylic salt groups for water-solubility.

Also useful herein are so-called carboxyvinyl polymers disclosed as toothpaste components in U.S. Pat. No. 3,980,767 to Chown et al; U.S. Pat. No. 3,935,306 to Roberts et al; U.S. Pat. No. 3,919,409 to Perla et al; U.S. Pat. No. 3,911,904 to Harrison, and U.S. Pat. No. 3,711,604 to Colodney et al. They are commercially available for example under the trademarks Carbopol 934, 940, 941, 907, 910, 934P and 956 of B. F. Goodrich, these products consisting essentially of a colloidally water-soluble polymer of polyacrylic acid crosslinked with from about 0.75% to about 2.0% of polyallyl sucrose or polyallyl pentaerythritol as cross linking agent. The AEA generally contributes to the viscosity of the oral gel composition and when cross-linked frequently possesses gelling or thickening properties. In this regard, Carbopol cross-linked polyacrylate is particularly desirable for inclusion to provide its gelling agent properties to the oral gel composition having a viscosity of about $200 \times 10^3$ to about $360 \times 10^3$ cps. When present, it is preferably present together with other AEA.

The AEA may also comprise natural anionic polymeric polycarboxylates containing retention-enhancing groups. Carboxymethyl cellulose and other binding agents gums and film-formers devoid of the above-defined delivery-enhancing and/or retention-enhancing groups are ineffective as AEA's.

As illustrative of AEA's containing phosphinic acid and/or sulfonic acid delivery enhancing groups, there may be mentioned polymers and copolymers containing units or moieties derived from the polymerization of vinyl or allyl phosphinic and/or sulfonic acids substituted as needed or the 1 or 2 (or 3) carbon atom by an organic retention-enhancing group, for example having the formula $-(X)_n-R$ defined above. Mixtures of these monomers may be employed, and copolymers thereof with one or more inert polymerizable ethylenically unsaturated monomers such as those described above with respect to the operative synthetic anionic polymeric polycarboxylates. As will be noted, in these and other polymeric AEA's operative herein, usually only one acidic delivery-enhancing group is bonded to any given carbon or other atom in the polymer backbone or branch thereon. Polysiloxanes containing pendant delivery-enhancing groups and retention enhancing groups may also be employed as AEA's herein. Also effective as AEA's herein are ionomers containing or modified to contain delivery- and retention-enhancing groups. Ionomers are described on pages 546–573 of the Kirk-Othmer Encyclopedia of Chemical Technology, third edition, Supplement Volume, John Wiley & Sons, Inc. copyright 1984, which description is incorporated herein by reference. Also effective as AEA's herein, provided they contain or are modified to certain retention-enhancing groups, are polyesters, polyurethanes and synthetic and natural polyamides including proteins and proteinaceous materials such as collagen, poly (argenine) and other polymerized amino acids.

The synthetic anionic polymeric polycarboxylate component is most often a hydrocarbon with optional halogen and O-containing substituents and linkages as present in for example ester, ether and OH groups, and is employed in the instant compositions in approximate weight amounts of 0.05 to 4% or more, preferably 0.1 to 3%, more preferably about 0.5 to 2.5%, e.g. about 0.5–1%.

The preferred AEA's are essentially straight chain and not highly cross-linked, such as the 1:4 copolymers of maleic anhydride or acid with a polymer of an ethylenically unsaturated monomer such as methyl vinyl ether sold as Gantrez S-97 and the like. For adherence to the titanium collar of dental implants, the preferred amount of such essentially straight AEA is about 0.5–1% by weight. Higher amounts of essentially straight chain AEA can reduce the viscosity of the oral gel composition, although compensation can be made for this by increasing the amount of gelling agents.

Without being bound to a theory, it is believed that the AEA, especially polymeric AEA is most often an anionic film forming material and is thought to attach to tooth surfaces and form a continuous film over the surfaces, thereby preventing bacterial attachment to tooth surfaces. It is possible that the noncationic antibacterial agent forms a complex or other form of association with the AEA, thus forming a film of a complex or the like over tooth surfaces. The enhanced delivery and film forming property of the AEA and the enhanced delivery and retention of the antibacterial agent on dental implant oral surfaces due to the AEA appears to make implant surfaces unfavorable for bacterial accumulation particularly since the direct bacteriostatic action of the antibacterial agent controls bacterial growth. Therefore, through the combination of three modes of actions: (1) enhanced delivery, (2) long retention time on dental implant oral surfaces, and (3) prevention of bacterial attachment to dental implant oral surfaces, the oral composition is made efficacious for reducing plaque. Similar antiplaque effectiveness is attained on soft oral tissue at or near the interface of implant and gum line.

In the present invention, the oral composition is a gel and is similar to a liquid dentifrice although more of a muco-adhesive, being somewhat more viscous (viscosity of about $150 \times 10^3$ to $360 \times 10^3$ cps, preferably about $200 \times 10^3$ to about $300 \times 10^3$ cps) then commercially available liquid dentifrice. Unlike a more liquid dentifrice, it does not readily flow from a package having an orifice about 0.05 to 0.15 mm diameter except with the application of mild mechanical pressure. Reference hereinto viscosity values as viscosity as determined with a Brookfield Digital Viscometer, having Spindle 95-Helipath Spindle at 5 rpm and room temperature (25° C.).

As indicated, the noncationic antibacterial agent is substantially water-insoluble. However, organic surface active agent, flavoring oil or mixtures thereof dissolve the antibacterial agent to assist it to reach soft oral tissue at or near the interface of dental implant and gums as well as the implant surfaces.

The oral gel composition contains as gelling agent a natural or synthetic thickener or gelling agent at the higher range of amounts which have been suggested for liquid dentifrices in view of its muco-adhesive properties, such as about 2–10% by weight, preferably about 2 to about 5%, to provide a viscosity for the oral gel composition of about $150 \times 10^3$ to about $360 \times 10^3$ cps, preferably about $200 \times 10^3$ to about $300 \times 10^3$ cps. A suitable thickener is synthetic hectorite, a synthetic colloidal magnesium alkali metal silicate complex clay available for example as Laponite (e.g. CP, SP 2002, D) marketed by Laporte Industries Limited. Laponite D analysis shows, approximately by weight, 58.00% SiO2, 25.40% MgO, 3.05% Na2O, 0.98% Li2), and some water and trace metals. Its true specific gravity is 2.53 and it has an apparent bulk density (g./ml. at 8% moisture) of 1.0. Carboxyvinyl polymers available from B. F. Goodrich as Carbopol are also used as thickeners or gelling agents since they are cross-linked polymers and indeed can be preferred, for instance Carbopol 934, 940, 907,910, 934P or Carbopol 956. As stated above Carbopol carboxyvinyl polymers can also be used as AEA's.

Other suitable thickeners or gelling agents include Irish moss, i-carrageenan, gum tragacanth, starch, polvinylpyrrolidone, hyudroxyethypropyl-cellulose, hydroxybutyl methyl cellulose, hydroxypropyl methyl cellulose, hydroxyethyl cellulose (e.g. available as Natrosol), sodium carboxymethyl cellulose and colloidal silica such as those available as finely ground Syloid (244) and Sylox.

Organic surface-active agents are also used in the compositions of the present invention to achieve increased prophylactic action, assist in achieving thorough and complete dispersion of the antiplaque antibacterial agent in the oral cavity, and render the instant compositions more cosmetically acceptable. The organic surface-active material is preferably anionic, nonionic or ampholytic in nature, and it is preferred to employ as the surface-active agent a detersive material which imparts to the composition detersive and foaming properties. Suitable examples of anionic surfactants are water-soluble salts of higher fatty acid monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2-dihydroxy propane sulfonate, higher fatty esters of taurine and the substantially saturated higher aliphatic acyl amides of lower aliphatic amino carboxylic acid compounds, such as those having 12 to 16 carbons in the fatty acid, alkyl or acyl radicals, and the like. Examples of the last mentioned taurines and amides are N-methyl-N-cocoyl taurate, N-methyl-N-oleoyl taurate, N-methyl-N-palmitoyl taurate, N-lauroyl sarcosine, and the sodium, potassium, and ethanolamine salts of N-lauroyl, N-myristoyl, or N-palmitoyl sarcosine which should be substantially free from soap or similar higher fatty acid material. The use of these sarcosinate compounds in the oral compositions of the present invention is particularly advantageous since these materials exhibit a prolonged and marked effect in the inhibition of acid formation in the oral cavity due to carbohydrate breakdown in addition to exerting some reduction in the solubility of tooth enamel in acid solutions. Examples of water-soluble nonionic surfactants are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly(ethylene oxide) with fatty acids, fatty alcohols, fatty amides, polyhydric alcohols (e.g. sorbitan monosterate) and polypropyleneoxide (e.g. Pluronic materials).

Surface active agent is typically present in amount of about 0.5–5% by weight, preferably about 0.7–2%. A desirable surface active mixture contains about 0.6% by weight sodium lauryl sulfate and about 0.25% by weight of sodium methyl cocoyl taurate.

If desired, a material additional to organic surface active agent and flavoring oil which assists in dissolving the noncationic antibacterial agent, particularly in the presence of saliva, may be present, to assist effective antiplaque delivery of the antibacterial agent, particularly to soft oral tissues at or near the gum line. Such effective solubilizing agent include humectant polyols such as propylene glycol, dipropylene glycol and hexylene glycol cellosolves such as methyl cellosolve and ethyl cellosolve, vegetable oils and waxes containing at least about 12 carbons in a straight chain such as olive oil, castor oil and petrolatum and esters such as amyl acetate, ethyl acetate and benzyl benzoate.

Significant amounts of polyethylene glycol particularly of molecular weight of 600 or more should be avoided since polyethylene glycol effectively inhibits the antibacterial activity of the noncationic antibacterial agent. For instance, polyethylene glycol (PEG) 600 when present with triclosan in a weight ratio of 25 triclosan: 1 PEG 600 reduces the antibacterial activity of triclosan by a factor of about 16 from that prevailing in the absence of the polyethylene glycol.

Because the gel composition is provided for direct application to a specific area in the oral cavity, that is a dental implant site, the oral gel composition typically does not contain a polishing agent.

Without being bound to a theory whereby the advantages of this invention are achieved, it is believed that an aqueous vehicle (typically, about 35–70% by weight water) typically including humectant (e.g. glycerine, sorbitol, xylitol and the like, including mixtures), is normally solubilized in surfactant micelles in a mouthwash or mobile phase (that is, not including gelling agent). Such solution during use becomes diluted with saliva but triclosan does not substantially precipitate and may be additionally protected against precipitation by presence of a solubilizing material such as propylene glycol. In this regard it is noted that propylene glycol is widely used in drug delivery systems for its strong interaction with biological membranes. It is expected that triclosan is partitioned from aqueous environment into propylene glycol and surfactant emulsions during use and further that propylene glycol in bulk phase allows greater probability of triclosan emergence out of surfactant micelles, thereby rendering triclosan available for delivery into bacterial and soft surfaces as well as onto tooth surfaces. Similar remarks apply to the other water-insoluble noncationic antibacterial agents herein described.

The oral gel composition may also contain an anticaries amount of fluoride ion source sufficient to supply 25 ppm. to 5,000 ppm. of fluoride ions. The fluoride ion source may be present even when the polyphosphate anticalculus agent is not, since it also provides anticaries effectiveness.

The sources of fluoride ions, or fluoride-providing component are well known in the art as anti-caries agents. These compounds may be slightly soluble in water or may be fully water-soluble. It is characterized by its ability to release fluoride ions in water and by substantial freedom from undesired reaction with other compounds of the oral preparation. Among these materials are inorganic fluoride salts, such as soluble alkali metal, alkaline earth metal salts, for example, sodium fluoride, potassium fluoride, ammonium fluoride, calcium fluoride, a copper fluoride such as cuprous fluoride, zinc fluoride, barium fluoride, sodium flourosilicate, ammonium flourosilicate, sodium fluorozirconate, ammonium fluorozirconate, sodium monofluorophosphate and aluminum mono-and di-fluorophosphate. Alkali metal and tin fluorides, such as sodium and stannous fluorides, sodium monofluorophosphate (MFP) and mixtures thereof, are preferred.

The amount of fluorine-providing compound is dependent to some extent upon the type of compound, its solubility, and the type of oral preparation, but it must be a non-toxic amount, generally about 0.0005 to about 3.0% in the preparation. In a dentifrice preparation, an amount of such compound which releases up to about 5,000 ppm of F ion by weight of the preparation is considered satisfactory. Any suitable minimum amount of such compound may be used, but it is preferable to employ sufficient compound to release about 300 to 2,000 ppm, more preferably 500 to 800 to about 1,500 ppm of fluoride ion.

Typically, in the cases of alkali metal fluorides, this component is present in an amount up to about 2% by weight, based on the weight of the preparation, and preferably in the range of about 0.05% to 1%. In the case of sodium monofluorophosphate, the compound may be present in an amount of about 0.1–3%, more typically 0.76%.

It will be understood that, as is conventional, the oral gel composition is to be sold or otherwise distributed in suitable labeled packages. Thus gel composition will usually be in a collapsible tube, typically aluminum, lined lead or plastic or in a syringe or other dispenser for metering out the contents upon application of mild mechanical pressure, having a label describing it, in substance, as an oral gel composition. When not sold or distributed in a syringe, a conventional syringe, typically holding about 2 to 10 cc of material is used separately from the otherwise packaged oral gel composition. Contents from such other package are extruded into the syringe in amount sufficient for one, several or many applications to dental implant areas. The syringe is held at or close to the dental implant and the oral gel composition is expelled onto implant and implant/gum interfaces, to permit delivery and retention of the noncationic antibacterial agent directly to these areas. Typically, about 0.2 to 0.5 gm of oral gel composition, preferably about 0.25 gm are delivered to each implant area with each application. Desirably the composition is applied at least once, to three or more times per day.

Various other materials may be incorporated in the oral preparations of this invention such as whitening agents, preservatives, silicones, chlorophyll compounds and/or ammoniated material such as urea, diammonium phosphate, and mixtures thereof. These adjuvants, where present, are incorporated in the preparations in amounts which do not substantially adversely affect the properties and characteristics desired. Significant amounts of zinc, magnesium and other metal salts and materials, generally soluble, which would complex with active components of the instant invention are to be avoided.

Any suitable flavoring or sweetening material may also be employed. Examples of suitable flavoring constituents are flavoring oils, e.g. phenolic flavoring oils, oil of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, xylitol, sodium cyclamate, perillartine, AMP (aspartyl phenyl alanine, methyl ester), saccharine and the like. Suitably, flavor and sweetening agents may each or together comprise from about 0.07% to 6% or more of the preparation, each being typically about 0.07–2.5%. Moreover the flavoring oil is believed to assist in dissolving the antibacterial agent. Xylitol and sorbitol can be used in larger amount for their humectant properties.

In the preferred practice of this invention an oral gel composition containing a composition of the present invention is preferably applied regularly to dental enamel and gums from a syringe such as every day or every second or third day or preferably from 1 to 3 times daily, at a pH of about 4.5 to about 9, generally about 5.5 to about 8, preferably about 6 to 8, for at least 2 weeks up to 8 weeks or as a permanent regimen.

The following examples are further illustrative of the nature of the present invention, but it is understood that the invention is not limited thereto. All amounts and proportions referred to herein and in the appended claims are by weight, unless otherwise indicated.

EXAMPLE 1

The oral gel composition below is prepared and introduced into a conventional 10 cc syringe by mechanical extraction from a plastic dentifrice tube having a circular orifice with a 0.15 mm diameter. Pressure is applied to the syringe to extrude about 0.25 gm of the oral gel composition onto dental implant area in the oral cavity including the interface of the implant and gum tissue. The oral gel composition applied in this manner is highly effective in reducing plaque in the dental implant area, compared to toothpaste containing equivalent amounts of Triclosan and AEA applied in conventional manner by toothbrushing.

ORAL GEL COMPOSITION

| | PARTS |
|---|---|
| Gantrez S-97 (13% Solution premixed with 50% sodium hydroxide to pH 6.8) | 6.75 (0.88 parts Gantrez S-97 on solids basis) |
| Glycerine | 15.0 |
| Propylene Glycol | 0.50 |
| Carbopol 934 Carboxyvinyl (Acrylic) Cross-Linked Copolymer | 3.5 |
| Sodium Lauryl Sulfate | 0.600 |
| Sodium Methyl Cocoyl Taurate (Tauranol) | 0.250 |
| Triclosan | 0.300 |
| Xylitol | 5.0 |
| Flavoring Oil | 0.100 |
| Sodium Hydroxide (10%) | 10.0 |
| Water | 58.0 |
| pH | 7.0 |
| Viscosity | $205 \times 10^3$–$240 \times 10^3$ cps |

EXAMPLE 2

| | PARTS |
|---|---|
| Gantrez S-97 (13% Solution premixed with 50% sodium hydroxide to pH 6.8) | 5.75 (0.75 parts Gantrez S-97 on solids basis) |
| Glycerine | 15.0 |
| Propylene Glycol | 0.50 |
| Carbopol 934 Carboxyvinyl (Acrylic) Cross-Linked Copolymer | 5.0 |
| Sodium Lauryl Sulfate | 0.600 |
| Sodium Methyl Cocoyl Taurate (Tauranol) | 0.250 |
| Triclosan | 0.30 |
| Xylitol | 6.0 |
| Flavoring Oil | 0.1 |
| Sodium Hydroxide (10%) | 12.0 |
| Water | 54.5 |
| pH | 6.4 |
| Viscosity | $300 \times 10^3$–$360 \times 10^3$ cps |

In the foregoing Examples improved results are also achieved when Triclosan is replaced with each of phenol, 2,2-methylene bis(4-chloro-6 Bromophenol), eugenol and thymol and/or when Gantarez is replaced by other AEA's such as styrene phosphonic acid copolymers having molecular weights within the range of about 3,000 to 10,000 such as poly (beta-styrenephosphonic acid), copolymers of vinyl phosphonic acid with beta-styrenephosphonic acid, and poly (alpha-styrenephosphonic acid), or sulfoacrylic oligomers, or a 1:1 copolymer of maleic anhydride with ethyl acrylate.

This invention has been described with respect to certain preferred embodiments and it will be understood that modifications and variations thereof obvious to those skilled in the art are to be included within the purview of this application and the scope of the appended claims.

We claim:

1. A process for attaching, adhering or bonding a plaque-inhibiting antibacterial agent to a dental implant area in the oral cavity, the implant being composed of a titanium alloy fixture affixed to alveolar bone, a titanium alloy collar transmucosal abutment at the gingiva mucosa surface where plaque tends to form and a porcelain prosthesis attached to said collar, which comprises placing an oral gel mucoadhesive composition in a dental syringe, which oral gel composition has a viscosity of about $150 \times 10^3$ to about $360 \times 10^3$ cps and comprises in an orally acceptable gel vehicle, an effective antiplaque amount of a substantially water insoluble noncationic antibacterial agent selected from the group consisting of halogenated diphenyl ethers, halogenated salicylanides, benzoic esters, halogenated carbanilides and phenolic compounds, at least one of an organic surface active agent and a flavoring oil solubilizing material for said antibacterial agent in amount sufficient to dissolve said antibacterial agent in saliva and about 0.005–6% by weight of an antibacterial-enhancing agent having utility as dentifrice or denture adhesive fixative or dental cement which contains at least one acidic delivery-enhancing functional group selected from the group consisting of carboxylic, phosphinic, phosphonic, and sulfonic acids, and their salts, and mixtures thereof and at least one organic retention-enhancing group, wherein said retention-enhancing group comprises the formula—$(X)_n$—R wherein X is O, N, S, SO, $SO_2$, P, PO or Si, R is hydrophobic alkyl, alkenyl, acyl, aryl, alkaryl, aralkyl, heterocyclic, or their inert-substituted derivatives, and n is zero or 1 or more and wherein said antibacterial enhancing agent is a natural or synthetic polymerizable monomer or a polymer selected from the group consisting of oligomers, homopolymers, copolymers of two or more monomers, ionomers, block copolymers, graft copolymers and crosslinked polymers and monomers, wherein said delivery-enhancing group enhances delivery of said antibacterial agent to oral dental implant and implant/gum surfaces by attaching or substantially adhesively, cohesively or otherwise bonding said antibacterial enhancing agent to said oral surfaces and said retention-enhancing group enhances attachment, adherence or bonding of said antibacterial agent to said antibacterial enhancing agent and indirectly to said oral surfaces, wherein said oral gel composition is free of polyphosphate anticalculus agent in an effective anticalculus amount, applying said syringe to a dental implant and extruding said oral gel composition from said syringe onto the surface of said implant including the interface of said dental implant with gum surfaces.

2. The process claimed in claim 1 wherein said antibacterial agent is a halogenated diphenyl ether.

3. The process claimed in claim 2 wherein said halogenated diphenyl ether is 2,4,4'-trichloro-2'-hydroxydiphenyl ether.

4. The process in claim 1 wherein said amount of antibacterial agent is about 0.01–0.6% by weight.

5. The process claimed in claim 1 wherein said surface active agent is present in amount of about 0.75–2% by weight.

6. The process claimed in claim 1 wherein said flavoring oil is present in amount of about 0.07–2.5% by weight.

7. The process according to claim 1 wherein said antibacterial-enhancing agent has an average molecular weight of about 100 to about 1,000,000.

8. The process claimed in claim 1 wherein said antibacterial-enhancing agent is an anionic polymer containing a plurality of said delivery-enhancing and retention-enhancing groups.

9. The process claimed in claim 8 wherein said anionic polymer comprising a chain containing repeating units each containing at least one carbon atom.

10. The process claimed in claim 9 wherein each unit contains at least one delivery-enhancing group and at least one organic retention-enhancing group bonded to the same or vicinal, or other atoms in the chain.

11. The process claimed in claim 10 wherein the delivery-enhancing group is carboxylic group or salt thereof.

12. The process claimed in claim 11 wherein the antibacterial-enhancing agent is a copolymer of maleic acid or anhydride with another ethylenically unsaturated polymerizable monomer.

13. The process claimed in claim 12 wherein said other monomer of said copolymer is methyl vinyl ether in a 4:1 to 1:4 molar ratio with the maleic acid or anhydride.

14. The process claimed in claim 13 wherein said copolymer has a molecular weight of about 30,000–1,000,000 and is present in amount of about 0.5–2.5% by weight.

15. The process claimed in claim 14 wherein the copolymer has an average molecular weight of about 70,000.

16. The process claimed in claim 14 wherein said oral gel composition comprises about 2–5% by weight a cross-linked carboxyvinyl polymer gelling agent.

17. The process claimed in claim 1 wherein said oral composition contains an effective anticaries amount of a fluoride ion-providing source.

* * * * *